(12) United States Patent
Mitani et al.

(10) Patent No.: US 12,558,031 B2
(45) Date of Patent: Feb. 24, 2026

(54) BIOLOGICAL INFORMATION MEASUREMENT DEVICE

(71) Applicant: Magnolia White Corporation, Tokyo (JP)

(72) Inventors: Hiromi Mitani, Tokyo (JP); Kei Tamura, Tokyo (JP); Masaki Murase, Tokyo (JP)

(73) Assignee: Magnolia White Corporation, Tokyo (JP)

( * ) Notice: Subject to any disclaimer, the term of this patent is extended or adjusted under 35 U.S.C. 154(b) by 220 days.

(21) Appl. No.: 18/418,528

(22) Filed: Jan. 22, 2024

(65) Prior Publication Data

US 2024/0245353 A1     Jul. 25, 2024

(30) Foreign Application Priority Data

Jan. 24, 2023     (JP) ................................. 2023-008790

(51) Int. Cl.
| | |
|---|---|
| *A61B 5/00* | (2006.01) |
| *A61B 5/0205* | (2006.01) |
| *A61B 5/024* | (2006.01) |
| *A61B 5/0531* | (2021.01) |
| *A61B 5/0533* | (2021.01) |
| *A61B 5/291* | (2021.01) |

(52) U.S. Cl.
CPC .......... *A61B 5/6803* (2013.01); *A61B 5/0205* (2013.01); *A61B 5/0059* (2013.01); *A61B 5/024* (2013.01); *A61B 5/0531* (2013.01); *A61B 5/291* (2021.01); *A61B 2560/0468* (2013.01); *A61B 2562/06* (2013.01)

(58) Field of Classification Search
CPC ......... A61B 5/256; A61B 5/291; A61B 5/369; A61B 5/6803; A61B 5/6814; A61B 5/0205; A61B 5/0059; A61B 5/024; A61B 5/0531; A61B 5/02416; A61B 5/0533
See application file for complete search history.

(56) References Cited

U.S. PATENT DOCUMENTS

| | | | | |
|---|---|---|---|---|
| 2023/0031613 A1* | 2/2023 | Fleury | .................. | A61B 5/6831 |
| 2024/0189589 A1* | 6/2024 | Wingeier | .............. | A61B 5/296 |
| 2024/0382132 A1* | 11/2024 | Yoshimizu | ........... | A61B 5/6814 |

FOREIGN PATENT DOCUMENTS

| | | | | |
|---|---|---|---|---|
| JP | 2021-045424 A | 3/2021 | | |
| KR | 102833039 B1 * | 7/2025 | ............. | A61B 5/265 |

* cited by examiner

*Primary Examiner* — Eun Hwa Kim
(74) *Attorney, Agent, or Firm* — K&L Gates LLP

(57)     ABSTRACT

A biological information measurement device including a housing having an annular structure and attachable to a subject, a first sensor including a first electrode, the first sensor detecting first biological information, a second sensor including a second electrode, the second sensor detecting second biological information different from the first biological information, a third sensor including a light receiving unit, the third sensor detecting third biological information different from the first biological information and the second biological information, and a ground electrode shared by the first sensor, the second sensor, and the third sensor is provided, wherein the first electrode, the second electrode, the light receiving unit, and the ground electrode are arranged to protrude in an inner direction of the housing.

6 Claims, 4 Drawing Sheets

FIG. 4

BIOLOGICAL INFORMATION MEASUREMENT DEVICE

CROSS-REFERENCE TO RELATED APPLICATIONS

This application claims the benefit of priority to Japanese Patent Application No. 2023-008790, filed on Jan. 24, 2023, the entire contents of which are incorporated herein by reference.

FIELD

The present disclosure relates to a biological information measurement device.

BACKGROUND

Conventionally, as one of biological sensors, an electroencephalograph sensor (EEG sensor) that measures an action potential of the brain is known. For example, Japanese Laid-Open Patent Publication No. 2021-45424 discloses a headset-type electroencephalograph measurement device including the EEG sensor.

SUMMARY

A biological information measurement device according to an embodiment of the present disclosure includes a housing having an annular structure and attachable to a subject, a first sensor including a first electrode, the first sensor detecting first biological information, a second sensor including a second electrode, the second sensor detecting second biological information different from the first biological information, a third sensor including a light receiving unit, the third sensor detecting third biological information different from the first biological information and the second biological information, and a ground electrode shared by the first sensor, the second sensor, and the third sensor, wherein the first electrode, the second electrode, the light receiving unit, and the ground electrode are arranged so as to protrude in an inner direction of the housing.

A biological information measurement device according to an embodiment of the present disclosure includes a housing having an annular structure, a first electrode of a first sensor detecting first biological information, a second electrode of a second sensor detecting second biological information different from the first biological information, a light receiving unit of a third sensor detecting third biological information different from the first biological information and the second biological information, and a ground electrode shared by the first sensor, the second sensor, and the third sensor, wherein the first electrode, the second electrode, the light receiving unit, and the ground electrode are arranged to protrude in an inner direction from an annulus of the housing.

BRIEF DESCRIPTION OF DRAWINGS

FIG. 4 is a functional block diagram of the biological information measurement device shown in FIG. 3.

DESCRIPTION OF EMBODIMENTS

Figure 1:
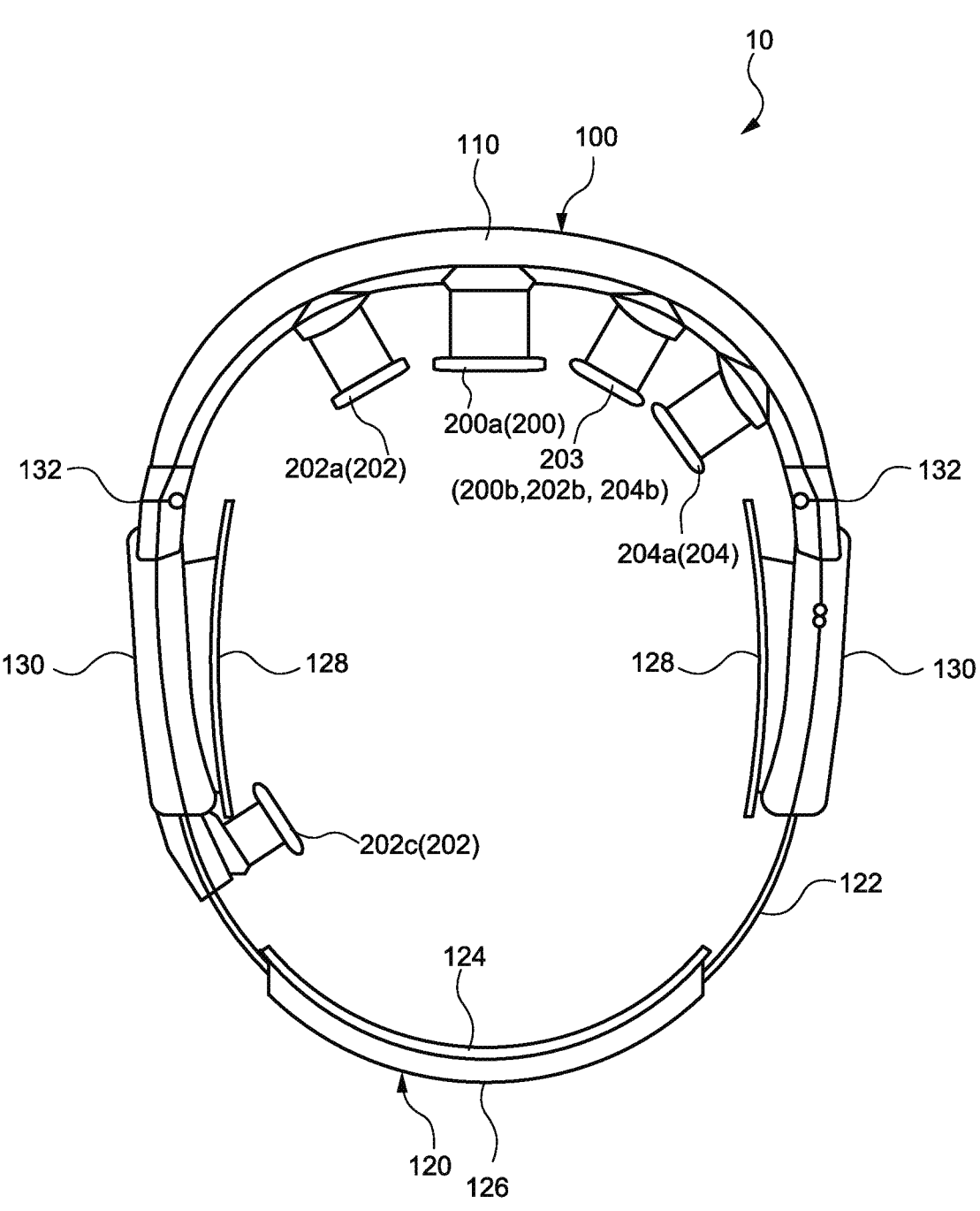
FIG. 1 is a schematic top view of a biological information measurement device according to an embodiment of the present disclosure.

Examples of the sensors other than the electroencephalograph sensor include an optical heart rate sensor (PPG sensor), which is a kind of heart rate sensor, and a galvanic skin response sensor (GSR sensor). The PPG sensor can obtain a pulse by emitting green light from an LED toward a blood vessel, detecting light reflected from the blood vessel, and measuring variation over time of the reflected light. The GSR sensor measures electric conductivity of skin. Since resistance of a current flowing through the skin decreases due to moisture in the skin, by measuring the electrical conductivity of the skin, it is possible to measure activity of a sympathetic nervous system from variation in amount of sweat secreted from sweat glands of a person.

Normally, in the case of measuring biological information, various sensors are arranged at respective measurement sites according to the biological information to be obtained. In the case where brain waves are measured by the EEG sensor, the measurement site is the head. In the case where a pulse is measured by the PPG sensor, a wrist where a thick blood vessel is present on a superficial side of the skin is often selected as the measuring site. In the case where the electric conductivity of the skin is measured by the GSR sensor, a palm or a fingertip is often selected as a measurement site. In the case where the biological information is obtained by using two or more kinds of biological sensors, it is necessary to attach the biological sensors at different measurement sites according to the kind of the biological sensors. Therefore, it takes time to attach the biological sensors. In addition, since the measurement site differs depending on the type of the biological sensor, there is a possibility that a variation occurs in the measurement result and accuracy of the biological information is deteriorated.

According to the present disclosure, it is possible to provide a biological information measurement device capable of reducing the time required for attachment of biological sensors at the time of measurement and improving accuracy of biological information obtained from a measurement result of each of the biological sensors by aggregating two or more kinds of biological sensors into one device.

Hereinafter, embodiments of the present invention will be described with reference to the drawings and the like. However, the present invention can be implemented in many different aspects, and should not be construed as being limited to the description of the embodiments exemplified below. In some cases, although the width, thickness, shape, and the like of each part are schematically represented in comparison with the actual embodiments in order to clarify the description, the drawings are merely examples and do not limit the interpretation of the present invention. In addition, in the present specification and the drawings, the same reference signs (or numbers followed by a, b, A, B, and the like) are given to the same elements as those described above with respect to the previous drawings, and detailed description thereof may be omitted as appropriate. Furthermore, the letters "first" and "second" with respect to the respective elements are convenient signs used to distinguish the respective elements, and do not have any further meaning unless otherwise specified.

As used herein, in the case where a member or region is referred to as being "above (or below)" another member or region, this includes not only the case where it is directly above (or directly below) the other member or region unless otherwise limited, but also the case where it is above (or below) the other member or region, that is, the case where another component is included between the other member or region.

Also, in the present specification, the expression "α includes A, B, or C," "α includes any of A, B or C," "α includes one selected from the group consisting of A, B and C," and the like does not exclude cases where α includes a plurality of combinations of A to C unless otherwise specified. Furthermore, these expressions do not exclude the case where α includes other elements.

First Embodiment

Figure 2:
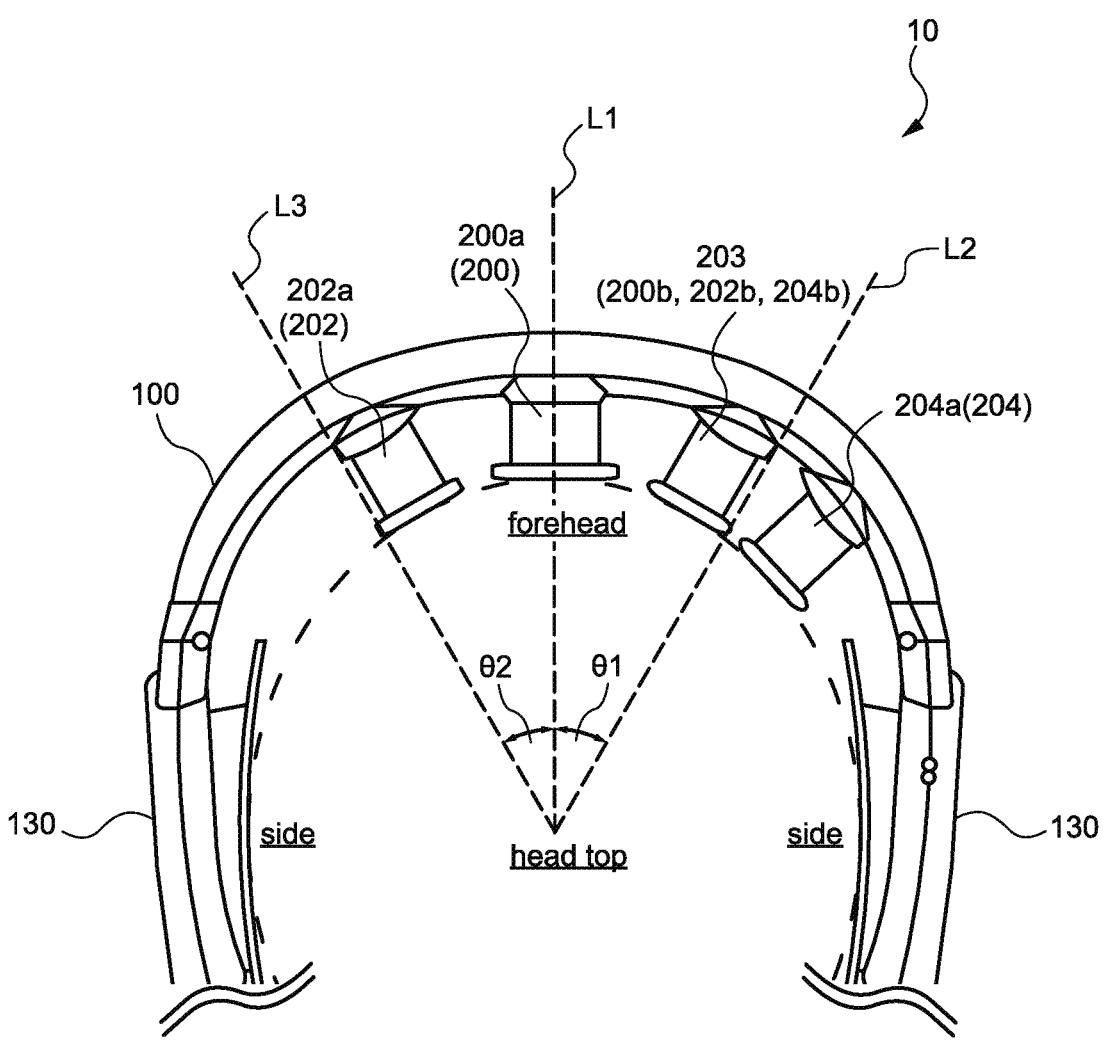
FIG. 2 is a partially enlarged view of the biological information measurement device shown in FIG. 1.

Referring to FIG. 1 and FIG. 2, a configuration of a biological information measurement device according to an embodiment of the present disclosure will be described.

FIG. 1 is a schematic top view of a biological information measurement device 10 according to a first embodiment of the present disclosure. The biological information measurement device 10 includes a housing 100, a first sensor 200, a second sensor 202, and a third sensor 204.

The housing 100 has a substantially annular structure (an annulus) along a forehead, a side and a back of the head of a wearer of the biological information measurement device 10. The housing 100 includes a front support part 110 and a rear support part 120.

The front support part 110 is located on the forehead side of the wearer wearing the biological information measurement device 10, and has a rounded shape that conforms to a shape of the forehead of the wearer. The front support part 110 is made of a flexible plastic material or the like. Further, although not shown, the front support part 110 may have a multi-layer structure including components made of different materials. For example, the front support part 110 may include an inner cover made of an elastic rubber material or the like, and an outer cover made of a flexible plastic material or the like.

The first sensor 200, the second sensor 202, and a third sensor 204 are attached to the front support part 110. The first sensor 200, the second sensor 202, and the third sensor 204 are attached to the front support part 110 so as to protrude in an inner direction of the housing 100. In other words, the first sensor 200, the second sensor 202, and the third sensor 204 protrude toward a wearing part of the wearer wearing the biological information measurement device 10. That is, the inner direction means a direction from the housing 100 toward the wearer. The first sensor 200, the second sensor 202, and the third sensor 204 will be described later.

The rear support part 120 is located on the back of the head side of the wearer wearing the biological information measurement device 10, and covers the back of the head from the side of the head of the wearer wearing the biological information measurement device 10. The rear support part 120 includes a rear band 122, a rear head support part 124, a band adjuster 126, a side head support part 128, a side housing 130, and a connector 132.

The rear head support part 124 contacts the back of the head of the wearer of the biological information measurement device 10. Two side head support parts 128 are provided, and each of the two side head support parts 128 contacts the side of the head of the wearer. The side head support parts 128 are coupled to respective side housings 130. The rear band 122 connects the rear head support part 124 and the two side housings 130 to each other. Each of the two side housings 130 is coupled to the front support part 110 via the connector 132. The connector 132 is provided with a hinge.

The band adjustor 126 can store and pull out the rear band 122. A user can shorten a length of the rear band 122 by storing the rear band 122 in the band adjustor 126. Conversely, the length of the rear band 122 can be increased by pulling the rear band 122 out of the band adjustor 126.

The two side housings 130 may house a CPU for processing detection signals output from the first sensor 200, the second sensor 202, and the third sensor 204, a board for wirelessly transmitting and receiving by such as Bluetooth, and a battery. For example, the CPU, the board, or the like may be housed by one side housing 130 of the two side housings 130, and the battery may be housed by the other side housing 130.

The rear support part 120 may be arranged with a part of the second sensor 202. As an example, the part of the second sensor 202 may be arranged adjacent to one side housing 130 as shown. Here, the part of the second sensor 202 is attached to the rear support part 120 so as to protrude in the inner direction of the housing 100. However, a position at which the part of the second sensor 202 is arranged in the rear support part 120 is not particularly limited, and is not limited to the position shown in FIG. 1.

The first sensor 200, the second sensor 202, and the third sensor 204 are attached to the front support part 110 of the housing 100. The first sensor 200, the second sensor 202, and the third sensor 204 are biological sensors for detecting different biological information. Types of the first sensor 200, the second sensor 202, and the third sensor 204 are not limited. In the present embodiment, the first sensor 200 is a PPG sensor, the second sensor 202 is an EEG sensor, and the third sensor 204 is a GSR sensor.

The first sensor 200 may be arranged substantially in a center of the front support part 110. As described above, the first sensor 200 is an optical PPG sensor. The PPG sensor can obtain a pulse by emitting light from an LED, detecting the light reflected from a blood vessel of the wearer, and measuring a variation with time of the reflected light. The first sensor 200 includes a light receiving unit 200a that detects light reflected from a blood vessel, and a grounded electrode (GND electrode) 203 (200b) to which a ground voltage (GND voltage) is provided. The GND electrode 203 (200b) may be arranged adjacently to the light receiving unit 200a. Although not shown, the first sensor 200 includes a light source that emits light toward the wearer.

The second sensor 202 may be arranged adjacently to the light receiving unit 200a of the first sensor 200. As described above, the second sensor 202 is an EEG sensor. The second sensor 202 includes an exploring electrode 202a, a GND electrode 203 (202b) and a reference electrode (REF electrode) 202c. The exploring electrode 202a and GND electrode 203 (202b) may be arranged so as to be positioned on both sides of the light receiving unit 200a of the first sensor 200 interposed therebetween. The REF electrode 202c may be arranged adjacently to one side housing 130 in the rear support part 120.

The third sensor 204 is a GSR sensor, as described above. The third sensor 204 includes two electrodes to which voltages of different potentials are respectively supplied. For example, the third sensor 204 may include an input electrode 204a to which a predetermined voltage is supplied, and a GND electrode 203 (204b). A position of the input electrode 204a of the third sensor 204 is not particularly limited. For example, the input electrode 204a may be arranged adjacently to the GND electrode 203 (204b) as shown in FIG. 1.

In this case, the input electrode 204a is arranged on a side opposite to a side on which the light receiving unit 200a of the first sensor 200 is located relative to the GND electrode 203 (204b). Further, although not shown, the input electrode 204a may be arranged at any position of the rear support part 120.

In the present embodiment, the GND electrodes 203 (200b, 202b, 204b) constituting the first sensor 200, the second sensor 202, and the third sensor 204 are the same. In other words, the GND electrode 203 as the GND electrode 200b of the first sensor 200 constitutes the first sensor 200 together with the light receiving unit 200a and a light source unit (not shown). Further, the GND electrode 203 as the GND electrode 202b of the second sensor 202 constitutes the second sensor 202 together with the exploring electrode 202a and the reference electrode 202c. Further, the GND electrode 203 as the GND electrode 204b of the third sensor 204 constitutes the third sensor 204 together with the input electrode 204a.

FIG. 2 is a partially enlarged view of the biological information measurement device 10 shown in FIG. 1. FIG. 2 is a diagram showing the biological information measurement device 10 viewed from the upper side of a head top of the wearer in the case where the user uses the biological information measurement device 10.

Positions at which the exploring electrode 202a of the second sensor 202 and GND electrode 203 (200b, 202b, 204b) are arranged are preferably within predetermined ranges from the light receiving unit 200a of the first sensor 200. As shown in FIG. 2, the head top of the wearer of the biological information measurement device 10 is set as a center, and a line L1 is set as a reference line which connects the head top and a position where substantially a center of the light receiving unit 200a of the first sensor 200 is located. In FIG. 2, a line L2 connecting the head top of the wearer and a position of 30° from the reference line L1 toward the right side of the wearer centering on the head top, and a line L3 connecting the head top of the wearer and a position of 30° from the reference line L1 toward the left side of the wearer centering on the top head are shown. In other words, an angle θ1 formed by the reference line L1 and the line L2 is 30°, and an angle θ2 formed by the reference line L1 and the line L3 is 30°. The exploring electrode 202a of the second sensor 202 and the GND electrode 203 (200b, 202b, 204b) are preferably arranged within 30° from the reference line L1 centering on the top head.

As described above, in the present embodiment, the GND electrode 203 (200b, 202b, 204b) is arranged between the reference line L1 and the line L2. Further, the exploring electrode 202a of the second sensor 202 is arranged between the reference line L1 and the line L3. In FIG. 1 and FIG. 2, the input electrode 204a of the third sensor 204 is arranged adjacently to the GND electrode 203 (200b, 202b, 204b). However, the input electrode 204a of the third sensor 204 may be arranged adjacently to the exploring electrode 202a of the second sensor 202. In this case, the input electrode 204a is arranged on a side opposite to a side on which the light receiving unit 200a of the first sensor 200 is located relative to the exploring electrode 202a.

In the present embodiment, the GND electrodes 203 (200b, 202b, 204b) of the first sensor 200, the second sensor 202, and the third sensor 204 are the same. By sharing one GND electrode 203 among the first sensor 200, the second sensor 202, and the third sensor 204, it is possible to reduce a number of electrodes and reduce burdens on the wearer when wearing the biological information measurement device 10. Further, by wearing the biological information measurement device 10, a plurality of different biological information can be acquired by simultaneously using a plurality of sensors.

Second Embodiment

Figure 3:
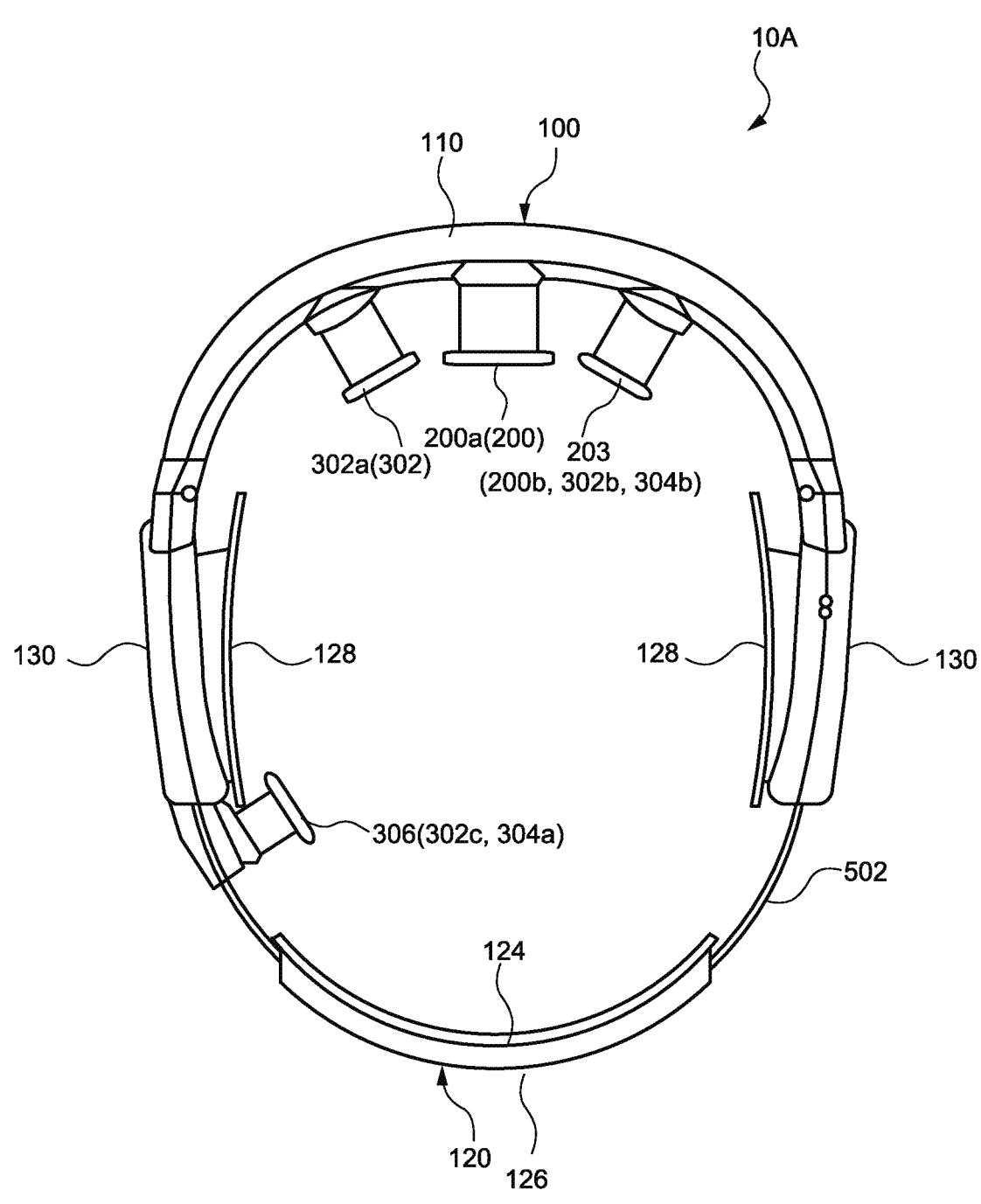
FIG. 3 is a schematic top view of a biometric information measurement device according to another embodiment of the present disclosure.
Figure 4:
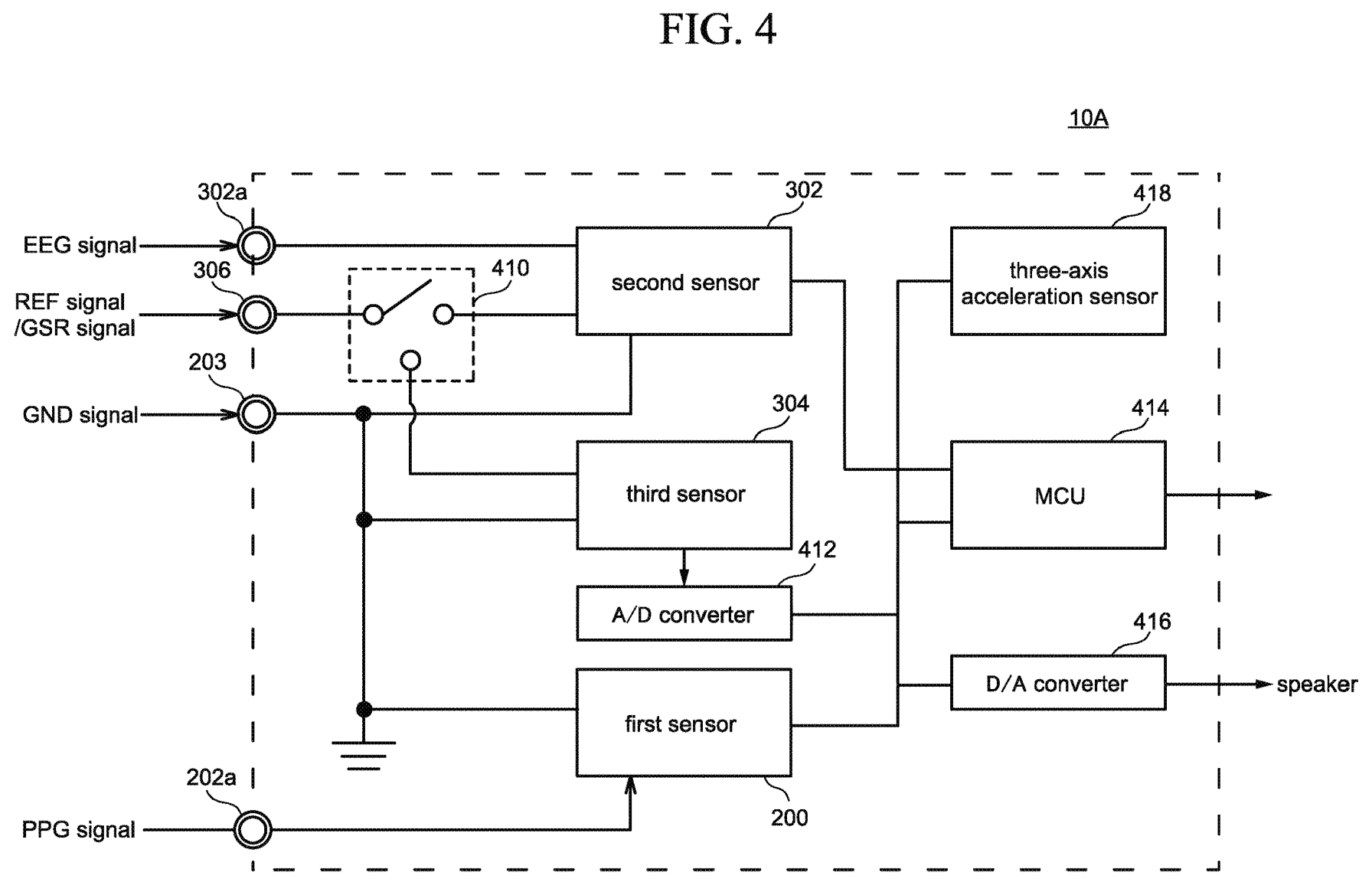

Referring to FIG. 3 and FIG. 4, a configuration of a biological information measurement device according to another embodiment of the present disclosure will be described.

FIG. 3 is a schematic top view of a biological data measurement device 10A according to a second embodiment of the present disclosure. The biological information measurement device 10A is substantially the same as the biological information device 10 according to the first embodiment described with reference to FIG. 1 and FIG. 2, except that configurations of a second sensor and a third sensor differ from the configurations of the second sensor 202 and the third sensor 204 in the first embodiment. Hereinafter, a second sensor 302 and a third sensor 304 of the biological information measurement device 10A according to the present embodiment will be mainly described, and configurations overlapping the biological information measurement device 10 of the first embodiment will not be described.

The biological data measurement device 10A includes the housing 100, the first sensor 200, the second sensor 302, and the third sensor 304. In the present embodiment, the first sensor 200, the second sensor 302, and the third sensor 304 are respectively a PPG sensor, an EEG sensor, and a GSR sensor, similarly to the first sensor 200, the second sensor 202 and the third sensor 204 of the biological information measurement device 10 according to the first embodiment.

In the present embodiment, the GND electrode 203 is common in the first sensor 200, the second sensor 302, and the third sensor 304, similarly to the first embodiment. In other words, the GND electrode 203 functions as the GND electrode 200b constituting the first sensor 200. The GND electrode 203 also functions as a GND electrode 302b constituting the second sensor 302. In addition, the GND electrode 203 also functions as a GND electrode 304b constituting the third sensor 304.

On the other hand, the biological data measurement device 10A according to the present embodiment includes a common electrode 306. The common electrode 306 functions as an REF electrode 302c of the second sensor 302 and an input electrode 304a of the third sensor 304. In other words, in the present embodiment, the REF electrode 302c of the second sensor 302 and the input electrode 304a of the third sensor 304 are the same.

The common electrode 306 functions as the REF electrode 302c of the second sensor 302 and the input electrode 304a of the third sensor 304 in a time division manner. That is, a driving period of the second sensor 302 is different from a driving period of the third sensor 304. If a driving period of the second sensor 202 is referred to as a first driving period and the driving period of the third sensor 304 is referred to as a second driving period, the first driving period and the second driving period do not overlap each other. During the first driving period, the common electrode 306 functions as the REF electrode 302c of the second sensor 302 and is supplied with a predetermined voltage. On the other hand, during the second driving period, the common electrode 306 functions as the input electrode 304a of the third sensor 304, and is supplied with a predetermined voltage. The predetermined voltage can be appropriately determined according to characteristics of a functioning sensor and an electrode. The predetermined voltage may be the same or different between the first driving period and the second driving period.

The common electrode 306 may be arranged adjacent to the one side housing 130 in the rear support part 120 of the housing 100. However, the position of the common electrode 306 is not limited thereto.

In the present embodiment, the first driving period during which the second sensor 302 is driven is different from the second driving period during which the third sensor 304 is driven. In other words, the second sensor 302 and the third sensor are driven in a time division manner. In the first driving period, the common electrode 306 can function as the REF electrode 302c of the second sensor 302, and in the second driving period, the common electrode 306 can function as the input electrode 304a of the third sensor 304. That is, the REF electrode 302c of the second sensor 302 and the input electrode 304a of the third sensor 304 can be shared. Accordingly, a number of electrodes attached to the biological information measurement device 10A can be further reduced.

Further, since the number of electrodes in the biological information measurement device 10A is reduced, as shown in FIG. 3, the light receiving unit 200a of the first sensor 200, an exploring electrode 302a of the second sensor 302, and the GND electrode 203 can be arranged in a well-balanced manner on the front support part 110 of the biological information measurement device 10A. Specifically, by arranging the light receiving unit 200a substantially at the center of the front support part 110 and arranging the exploring electrode 302a and the GND electrode 203 adjacent to the light receiving unit 200a within a predetermined range from the light receiving unit 200a, the arrangement of the electrodes can be substantially bilaterally symmetrical in the front support part 110.

In addition, the exploring electrode 302a of the second sensor 302 and the GND electrode 203 are same as the first embodiment, the head top of the wearer of the biological information measurement device 10A is set as a center, and if the line L1 connecting the head top and a position where a substantially center of the light receiving unit 200a of the first sensor 200 is located is taken as a reference line, the exploring electrode 302a of the second sensor 302 and the GND electrode 203 are preferably arranged within 30° from the reference line L1 centering on the head top.

In the present embodiment, the arrangement of the electrodes in the front support part 110 is substantially symmetrical, so that when the wearer wears the biological information measurement device 10A, the pressure applied to the forehead of the wearer, that is, pressing pressure of the electrodes is substantially uniform. As a result, a contact between each electrode in the front support part 110 and the forehead of the wearer is stabilized, and noise in measurement results by the second sensor 302 and the third sensor 304 is reduced, thereby reliability of the measurement results is improved.

FIG. 4 is a functional diagram of the biological data measurement device 10A according to the present embodiment. Referring to FIG. 4, the biological information measurement device 10A includes the first sensor 200, the second sensor 302, and the third sensor 304, as well as a selection switch 410, an A/D converter 412, an MCU 414, a D/A converter 416, and a three-axis acceleration sensor 418. The A/D converter 412, the MCU 414, the D/A converter 416, and the three-axis acceleration sensor 418 may be housed in the side housing 130 of the rear support part 120. By providing the three-axis acceleration sensor 418, for example, it is possible to detect not only a movement of the subject in only one direction but also a three-dimensional movement in an X direction, a Y direction, and a Z direction.

Since the first sensor 200, the second sensor 302, and the third sensor 304 are the same as described above, redundant description will be omitted.

A PPG signal for driving the first sensor 200 is applied to the first sensor 200. The PPG signal is provided to the light receiving unit 200a of the first sensor 200 together with a ground signal (GND signal) to be described later.

An EEG signal is applied to the exploring electrode 302a of the second sensor 302.

The GND signal is applied to the GND electrode 203. As described above, the GND electrode 203 commonly functions as the GND electrode 200b of the first sensor 200, the GND electrode 302b of the second sensor 302, and the GND electrode 304b of the third sensor 304.

An REF signal and a GSR signal are applied to the common electrode 306. The REF signal is provided to the common electrode 306 during the first driving period. In other words, during the first driving period, the common electrode 306 functions as the REF electrode 302c of the second sensor 302. On the other hand, the GSR signal is provided to the common electrode 306 during the second driving period that differs from the first driving period. In other words, the common electrode 306 functions as the input electrode 304a of the third sensor 304 during the second driving period.

The common electrode 306 is connected to the selection switch 410. A selection signal is applied to the selection switch 410. The selection switch 410 switches a connection destination of the common electrode 306 in accordance with the applied selection signal. Specifically, the selection switch 410 connects the common electrode 306 and the second sensor 302 during the first driving period, and the common electrode 306 functions as the REF electrode 302c of the second sensor 302. On the other hand, the selection switch 410 connects the common electrode 306 and the third sensor 304 during the second driving period, and the common electrode 306 functions as the input electrode 304a of the third sensor 304.

Measurement results obtained by the first sensor 200 and the second sensor 302 are output to the MCU 414. The measurement result by the third sensor 304 is digitally converted by the A/D converter 412 and then output to the MCU 414.

The MCU 414 may comprise a wireless communication circuit of BLE. The measurement results supplied to the MCU 414 may be transmitted by the BLE to an external device.

In addition, the measurement results by the first sensor 200 and the second sensor 302 may be output to the D/A converter 416. The measurement result by the third sensor 304 may be digitally converted by the A/D converter 412 and then output to the D/A converter 416. The D/A converter 416 may convert the provided measurement results into analog and transmit them to an external speaker.

Those in which a person skilled in the art appropriately adds, deletes, or changes in design of the constituent elements based on the configuration shown in the embodiments of the present disclosure described above, or omits or changes in conditions, are also included in the scope of the invention as long as the gist of the present disclosure is provided.

It is to be understood that even if there are other operational effects which are different from the operational effects provided by the aspects of the embodiments described above, those that are obvious from the description of the present embodiment, or those that can be easily predicted by a person skilled in the art is naturally provided by an embodiment of the present disclosure.

What is claimed is:

1. A biological information measurement device comprising:

a housing having an annular structure including a front support part configured to correspond to a forehead of a subject and a back support part configured to correspond to a back side of the head of the subject;

a first sensor is an electroencephalographic (EEG) sensor including a first electrode which functions as an active electrode;

a second sensor is a galvanic skin response (GSR) sensor including a second electrode configured to supply a predetermined voltage;

a third sensor is a photoplethysmographic (PPG) sensor including a light receiving unit; and a ground electrode configured to provide a ground voltage to the EEG sensor, the GSR sensor and the PPG sensor;

wherein the first electrode, the second electrode, the light receiving unit, and the ground electrode are arranged to protrude from an inner surface of the housing; and wherein the first electrode and the ground electrode are symmetrically arranged about the light receiving unit along the front support part.

2. The biological information measurement device according to claim 1, wherein:

the first sensor includes a contact electrode; and the second electrode and the contact electrode share a common electrode.

3. The biological information measurement device according to claim 1, wherein a second electrode of the EEG sensor operates as a reference electrode during the EEG measurement.

4. The biological information measurement device according to claim 1, wherein:

the light receiving unit is arranged substantially at a center of the front support part; and the first electrode and the ground electrode are arranged within a predetermined range from a position of the light receiving unit.

5. The biological information measurement device according to claim 4, wherein a direction of protrusion of light receiving unit from the inner surface of the housing and a direction of protrusion of the first electrode from the inner surface form an angle that is within 30°.

6. The biological information measurement device according to claim 1, wherein: the light receiving unit is arranged substantially at a center of the front support part; and the second electrode is arranged in the back support part.

* * * * *